United States Patent
Mitchell

(10) Patent No.: US 11,193,341 B2
(45) Date of Patent: Dec. 7, 2021

(54) REAL TIME MEASUREMENT OF GAS CONTENT IN DRILLING FLUIDS

(71) Applicant: Halliburton Energy Services, Inc., Houston, TX (US)

(72) Inventor: Ian David Campbell Mitchell, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 382 days.

(21) Appl. No.: 14/890,670

(22) PCT Filed: Sep. 25, 2013

(86) PCT No.: PCT/US2013/061668
§ 371 (c)(1),
(2) Date: Nov. 12, 2015

(87) PCT Pub. No.: WO2015/047247
PCT Pub. Date: Apr. 2, 2015

(65) Prior Publication Data
US 2016/0102510 A1    Apr. 14, 2016

(51) Int. Cl.
*E21B 21/00* (2006.01)
*E21B 49/00* (2006.01)
(Continued)

(52) U.S. Cl.
CPC .............. *E21B 21/00* (2013.01); *E21B 44/02* (2013.01); *E21B 47/113* (2020.05);
(Continued)

(58) Field of Classification Search
CPC ........ E21B 21/00; E21B 44/02; E21B 47/102; E21B 49/005; E21B 21/274;
(Continued)

(56) References Cited

U.S. PATENT DOCUMENTS 4,618,939 A    10/1986 Davis
5,027,267 A    6/1991 Pitts et al.
(Continued)

FOREIGN PATENT DOCUMENTS

CN    1904310 A    1/2007
CN    102334024 A    1/2012
(Continued)

OTHER PUBLICATIONS

International Search Report and Written Opinion for PCT/US2013/061668 dated Jul. 4, 2014.
(Continued)

*Primary Examiner* — Waseem Moorad
*Assistant Examiner* — Neel Girish Patel
(74) *Attorney, Agent, or Firm* — Gilliam IP PLLC

(57) ABSTRACT

Disclosed are systems and methods for monitoring drilling fluids in real time. One method includes circulating a drilling fluid into and out of a borehole, generating a first output signal with a first optical computing device arranged near an outlet of the borehole, the first optical computing device having a first integrated computational element configured to optically interact with the drilling fluid, receiving the first output signal with a signal processor communicably coupled to the first optical computing device, determining the concentration of a gas present in the drilling fluid at the outlet of the borehole with the signal processor and generating a resulting output signal, conveying the resulting output signal to one or more peripheral devices, and adjusting one or more drilling or completion parameters in response to the concentration of the gas present in the drilling fluid.

20 Claims, 7 Drawing Sheets

(51) Int. Cl.
| | |
|---|---|
| *G01N 33/28* | (2006.01) |
| *G01N 21/27* | (2006.01) |
| *G01N 21/85* | (2006.01) |
| *E21B 47/113* | (2012.01) |
| *E21B 44/02* | (2006.01) |
| *G01N 33/00* | (2006.01) |

(52) U.S. Cl.
CPC ......... *E21B 49/005* (2013.01); *G01N 21/274* (2013.01); *G01N 21/8507* (2013.01); *G01N 33/004* (2013.01); *G01N 33/0036* (2013.01); *G01N 33/0044* (2013.01); *G01N 33/2823* (2013.01)

(58) Field of Classification Search
CPC ............. E21B 21/8507; E21B 33/0036; E21B 33/004; E21B 33/0044; E21B 33/2823
See application file for complete search history.

(56) References Cited

U.S. PATENT DOCUMENTS

| | | | |
|---|---|---|---|
| 5,167,149 A | 12/1992 | Mullins et al. | |
| 5,400,137 A | 3/1995 | Winslow et al. | |
| 5,418,614 A | 5/1995 | Brost et al. | |
| 5,489,977 A | 2/1996 | Winslow et al. | |
| 5,859,430 A | 1/1999 | Mullins et al. | |
| 6,176,323 B1 * | 1/2001 | Weirich | E21B 21/08 175/40 |
| 6,198,531 B1 | 3/2001 | Myrick et al. | |
| 6,529,276 B1 | 3/2003 | Myrick | |
| 6,614,360 B1 * | 9/2003 | Leggett, III | E21B 44/00 340/853.1 |
| 7,123,844 B2 | 10/2006 | Myrick | |
| 7,138,156 B1 | 11/2006 | Myrick et al. | |
| 7,219,729 B2 | 5/2007 | Bostick, III et al. | |
| 7,472,748 B2 | 1/2009 | Gdanski et al. | |
| 7,623,233 B2 | 11/2009 | Freese et al. | |
| 7,697,141 B2 | 4/2010 | Jones et al. | |
| 7,712,527 B2 | 5/2010 | Roddy | |
| 7,834,999 B2 | 11/2010 | Myrick et al. | |
| 7,911,605 B2 | 3/2011 | Myrick et al. | |
| 7,920,258 B2 | 4/2011 | Myrick et al. | |
| 7,938,175 B2 | 5/2011 | Skinner et al. | |
| 8,049,881 B2 | 11/2011 | Myrick et al. | |
| 8,132,452 B1 * | 3/2012 | Selman | E21B 21/067 166/250.01 |
| 8,141,633 B2 | 3/2012 | Hampton et al. | |
| 8,212,213 B2 | 7/2012 | Myrick et al. | |
| 8,212,216 B2 | 7/2012 | Perkins et al. | |
| 8,213,006 B2 | 7/2012 | Myrick et al. | |
| 8,237,920 B2 | 8/2012 | Jones et al. | |
| 2006/0027144 A1 | 2/2006 | Chatterji et al. | |
| 2006/0142955 A1 * | 6/2006 | Jones | E21B 47/102 702/32 |
| 2007/0282647 A1 | 12/2007 | Freese et al. | |
| 2008/0231849 A1 | 9/2008 | Myrick et al. | |
| 2008/0276687 A1 | 11/2008 | Myrick et al. | |
| 2009/0073433 A1 | 3/2009 | Myrick et al. | |
| 2009/0097024 A1 | 4/2009 | Blackburn et al. | |
| 2009/0140144 A1 | 6/2009 | Myrick et al. | |
| 2009/0182693 A1 | 7/2009 | Fulton et al. | |
| 2009/0216504 A1 | 8/2009 | Priore et al. | |
| 2009/0219512 A1 | 9/2009 | Myrick et al. | |
| 2009/0219538 A1 | 9/2009 | Myrick et al. | |
| 2009/0219539 A1 | 9/2009 | Myrick et al. | |
| 2009/0250613 A1 | 10/2009 | Myrick et al. | |
| 2009/0299946 A1 | 12/2009 | Myrick et al. | |
| 2009/0316150 A1 | 12/2009 | Myrick et al. | |
| 2010/0012316 A1 | 1/2010 | Schlachter | |
| 2010/0050905 A1 | 3/2010 | Lewis et al. | |
| 2010/0051266 A1 | 3/2010 | Roddy et al. | |
| 2010/0051275 A1 | 3/2010 | Lewis et al. | |
| 2010/0073666 A1 | 3/2010 | Perkins et al. | |
| 2010/0141952 A1 | 6/2010 | Myrick et al. | |
| 2010/0148785 A1 | 6/2010 | Schaefer et al. | |
| 2010/0149537 A1 | 6/2010 | Myrick et al. | |
| 2010/0153048 A1 | 6/2010 | Myrick et al. | |
| 2010/0182600 A1 | 7/2010 | Freese et al. | |
| 2010/0186955 A1 | 7/2010 | Saasen et al. | |
| 2010/0195105 A1 | 8/2010 | Myrick et al. | |
| 2010/0245096 A1 | 9/2010 | Jones et al. | |
| 2010/0265509 A1 | 10/2010 | Jones et al. | |
| 2010/0302539 A1 | 12/2010 | Myrick et al. | |
| 2010/0305741 A1 | 12/2010 | Myrick | |
| 2010/0328669 A1 | 12/2010 | Myrick et al. | |
| 2011/0108720 A1 | 5/2011 | Ford et al. | |
| 2011/0132606 A1 | 6/2011 | Demong et al. | |
| 2011/0139464 A1 * | 6/2011 | Henderson | E21B 21/01 166/370 |
| 2011/0192594 A1 | 8/2011 | Roddy et al. | |
| 2011/0199610 A1 | 8/2011 | Myrick et al. | |
| 2011/0308788 A1 | 12/2011 | Ravi et al. | |
| 2012/0037428 A1 * | 2/2012 | Plop | E21B 7/062 175/61 |
| 2012/0150451 A1 * | 6/2012 | Skinner | G01N 33/2823 702/24 |
| 2012/0158310 A1 * | 6/2012 | Adams | E21B 47/06 702/13 |
| 2012/0181420 A1 | 7/2012 | Duncan et al. | |
| 2012/0191354 A1 * | 7/2012 | Caycedo | E21B 47/022 702/9 |
| 2012/0205103 A1 | 8/2012 | Ravi et al. | |
| 2012/0222852 A1 | 9/2012 | Pelletier | |
| 2013/0031964 A1 | 2/2013 | Tunheim et al. | |
| 2013/0032345 A1 * | 2/2013 | Freese | C09K 8/72 166/279 |
| 2013/0032545 A1 * | 2/2013 | Freese | C02F 1/008 210/739 |
| 2013/0213638 A1 | 8/2013 | Keller et al. | |
| 2013/0284901 A1 * | 10/2013 | Freese | G01N 21/17 250/208.2 |
| 2013/0284904 A1 * | 10/2013 | Freese | G01N 21/17 250/214 DC |

FOREIGN PATENT DOCUMENTS

| | | |
|---|---|---|
| EP | 1057118 B1 | 8/1999 |
| EP | 2491227 A1 | 8/2012 |
| JP | 2007-535655 A | 12/2007 |
| JP | 2009-524814 A | 7/2009 |
| WO | 2011049571 A1 | 4/2011 |
| WO | 2015047247 A1 | 4/2015 |

OTHER PUBLICATIONS

Chinese Application Serial No. 2013800790136; Second Office Action; dated Aug. 17, 2018, 4 pages.
Chinese Application Serial No. 2013800790136; Third Office Action; dated Dec. 25, 2018, 6 pages.
Chinese Application Serial No. 2013800790136; Office Action 4; dated Mar. 21, 2019, 6 pages.
India Application Serial No. 201617004711, Office Action, dated May 28, 2019, 6 pages.
Mexican Application Serial No. MX/a/2016/001841; First Office Action; dated Apr. 10, 2019, 4 pages.
GB Application Serial No. GB1602456.4, Examination Report Under Section 18(3), dated Nov. 12, 2019, 3 pages.
PCT Application Serial No. PCT/US2014/052627, International Search Report, dated May 27, 2015, 3 pages.
PCT Application Serial No. PCT/US2014/052627, Written Opinion, dated May 27, 2015, 11 pages.
PCT Application Serial No. PCT/US2014/052640, International Search Report, dated May 27, 2015, 3 pages.
PCT Application Serial No. PCT/US2014/052640, Written Opinion, dated May 27, 2015, 10 pages.
U.S. Appl. No. 15/313,266, Non-Final Rejection, dated Nov. 28, 2018, 10 pages.
U.S. Appl. No. 15/313,283, Non-Final Rejection, dated Nov. 16, 2018, 8 pages.

(56) References Cited

OTHER PUBLICATIONS

U.S. Appl. No. 16/535,292, Non-Final Office Action, dated Nov. 25, 2020, 11 pages.
China Application Serial No. 201380079013.6; China Search; Jan. 10, 2018, 1 page.
U.S. Appl. No. 16/535,292; Final Office Action: dated Mar. 8, 2021, 12 pages.
United Kingdom Application Serial No. 1621914.9; Examination Report, dated May 14, 2020, 2 pages.
U.S. Appl. No. 16/535,292; Corrected Notice of Allowability; dated Jun. 1, 2021, 3 pages.
U.S. Appl. No. 16/535,292: Notice of Allowance; dated May 3, 2021, 6 pages.
China Application Serial No. 201380079013.6; First Office Action; dated Jan. 19, 2018, 13 pages with English translation.
Brooke, et al., "Multimode Imaging in the Thermal Infrared for Chemical Contrast Enhancement. Part 1: Methodology", Anal. Chem., 2010, 82 (20), pp. 8412-8420, DOI: 10.1021/ac101109w, Sep. 23, 2010.
Brooke, et al., "Multimode Imaging in the Thermal Infrared for Chemical Contrast Enhancement. Part 2: Simulation Driven Design", Anal. Chem., 2010, 82 (20), pp. 8421-8426, DOI: 10.1021/ac101108z., Sep. 23, 2010.
Brooke, et al., "Multimode Imaging in the Thermal Infrared for Chemical Contrast Enhancement. Part 3: Visualizing Blood on Fabrics", Anal Chem., 2010, 82 (20), pp. 8427-8431, DOI: 10.1021/ac101107v., Sep. 23, 2010.
Brost, et al., "Optical Methods for Monitoring Treating Chemicals in Oilfield Water Systems", Society of Petroleum Engineers, 1991, 16 pages.
Dai, et al., "Molecular Factor Computing for Predictive Spectroscopy", Pharmaceutical Research, 2007, 10 pages.
Dai, "Simulations-Guided Design of Process Analytical Sensor Using Molecular Factory Computing", University of Kentucky Doctoral Dissertations, Paper 483, 2007, 204 pages.
Myrick, et al., "Spectral Tolerance Determination for Multivariate Optical Element Design", Fresenuis Journal of Analytical Chemistry, 369, Mar. 2001, pp. 351-355.
Ramchandran, et al., "Chemical Kinetics in Real Time: Using the Differential Rate Law and Discovering the Reaction Orders", A Physical Chemistry Laboratory Experiment, Journal of Chemical Education, 1996, pp. 686-689.
Simcock, et al., "Tuning D* with Modified Thermal Detectors", Applied Spectroscopy, vol. 60, No. 12, https://doi.org/10.1366/000370206779321481, 2006, pp. 1469-1476.
Soyemi, et al., "Design and Testing of a Multivariate Optical Element: The First Demonstration of Multivariate Optical Computing for Predictive Spectroscopy", Analytical Chemistry, vol. 73, No. 6, Mar. 15, 2001, pp. 1069-1079.

\* cited by examiner

REAL TIME MEASUREMENT OF GAS CONTENT IN DRILLING FLUIDS

BACKGROUND

The present disclosure relates to systems and methods for monitoring drilling fluids and, more specifically, for measuring the gas content in drilling fluids in real time using optical computing devices and adjusting one or more drilling parameters in response thereto.

During the drilling of a hydrocarbon-producing well, a drilling fluid or "mud" is continuously circulated from the surface down to the bottom of the wellbore being drilled and back to the surface again. The drilling fluid serves several functions, one of them being to transport wellbore cuttings up to the surface where they are separated from the drilling fluid. Another function of the drilling fluid is to cool the drill bit and provide hydrostatic pressure on the walls of the drilled borehole to prevent wellbore collapse and the resulting influx of gas or liquid from the formations being drilled.

Analyzing the drilling fluid as it returns to the surface is recognized in the oil and gas industry as an important first appraisal of a potential hydrocarbon-bearing reservoir zone, thereby providing important data to guide subsequent evaluation and testing. Such analysis and testing is commonly referred to as "mud logging" analysis. Through mud logging, reservoir zones can be evaluated while they are being initially penetrated, thereby substantially preventing post-drilling changes to the formation that can limit the effectiveness of many other evaluation techniques.

Mud logging often includes the measurement and analysis of formation gases present in the drilling fluid as it returns to the surface. Such analysis can be valuable in providing data on the hydrocarbon and non-hydrocarbon gas species that may be encountered while drilling. Specifically, knowing the presence and concentration of hydrocarbon and non-hydrocarbon gases in drilling fluids provides an indication of the formation confronted by the drill bit and provides a basis for determining the feasibility of obtaining hydrocarbons from the well. The information that such analysis provides is vital in the planning and development of hydrocarbon reservoirs, as well as in the assessment of a reservoir's capacity and performance.

Mud logging analysis of drilling fluids is typically conducted off-line using laboratory analyses which require the extraction of a sample of the drilling fluid and a subsequent controlled testing procedure usually conducted at a separate location. Depending on the analysis required, however, such an approach can take hours to days to complete, and even in the best case scenario, a job will often be completed prior to the analysis being obtained. Although off-line, retrospective analyses can be satisfactory in certain cases, they nonetheless do not allow real-time or near real-time analysis capabilities. As a result, proactive control of drilling operations cannot take place, at least without significant process disruption occurring while awaiting the results of the analysis. Off-line, retrospective analyses can also be unsatisfactory for determining true characteristics of a drilling fluid since the characteristics of the extracted sample of the drilling fluid often changes during the lag time between collection and analysis, thereby making the properties of the sample non-indicative of the true chemical composition or characteristic.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
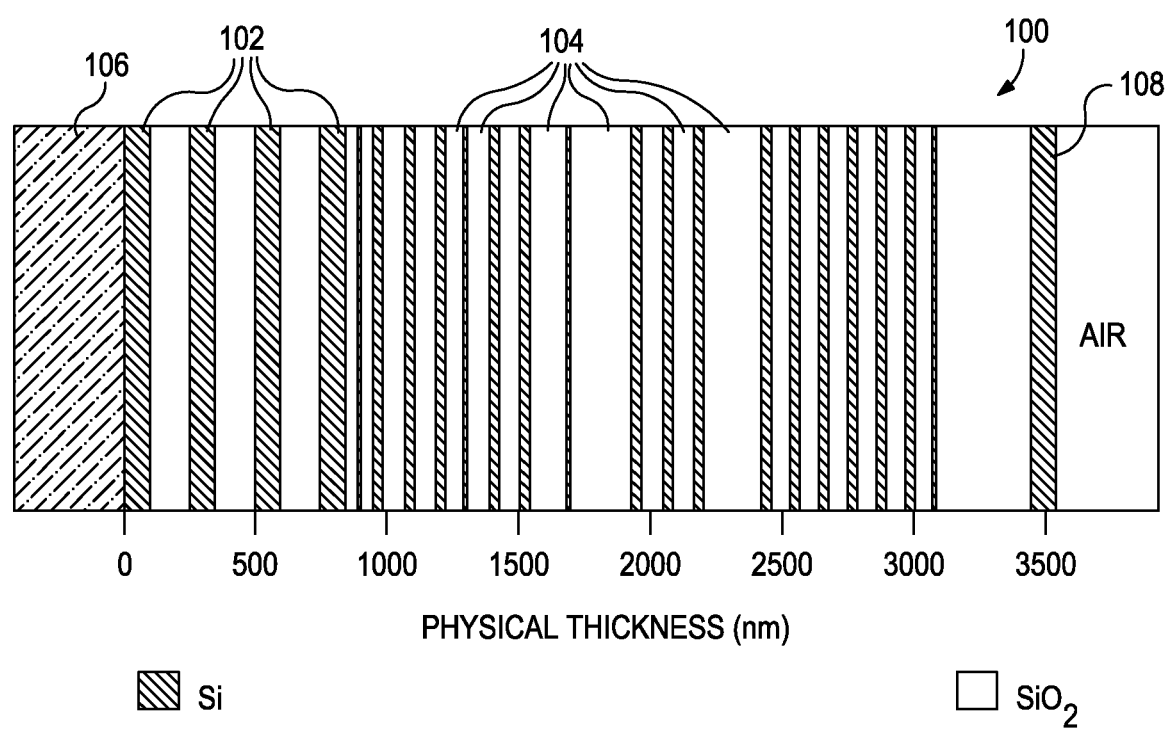
FIG. 1 illustrates an exemplary integrated computation element, according to one or more embodiments.

The present disclosure relates to systems and methods for monitoring drilling fluids and, more specifically, for measuring the gas content in drilling fluids in real time using optical computing devices and adjusting one or more drilling parameters in response thereto.

The exemplary systems and methods described herein employ various configurations and arrangements of optical computing devices, also commonly referred to as "opticoanalytical devices," for the real-time or near real-time monitoring of a fluid, such as a drilling fluid. In operation, the exemplary systems and methods may be useful and otherwise advantageous in determining one or more properties or characteristics of the fluid, such as the type and concentration of one or more gases present within the fluid. The optical computing devices can advantageously provide real-time fluid monitoring that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid, thereby allowing qualitative and/or quantitative analyses of the fluid to occur without having to extract a sample and undertake time-consuming analyses of the sample at an off-site laboratory.

The systems and methods disclosed herein may be suitable for use in the oil and gas industry since the described optical computing devices provide a cost-effective, rugged, and accurate means for monitoring oil/gas-related fluids, such as drilling fluids. In particular, the systems and methods may prove advantageous for use in mud logging gas analysis, thereby providing a stream of continuous data on the hydrocarbon and non-hydrocarbon gas species that may be encountered while drilling boreholes for the exploitation of hydrocarbon reserves below the earth's surface. When the drilling fluid returns to the surface, for example, it may contain hydrocarbons (and other compounds) contained within the rock that has been drilled as well as additional hydrocarbons that have leaked into the wellbore from the surrounding rock formation. The real-time measurement of the abundance of these gas compounds will yield information on the hydrocarbon content of the rock.

Such data may be provided to a well operator for interpretation and consideration and, if required, the well operator may alter various drilling or completion parameters in response thereto. For instance, depending on what types and concentrations of gases are detected within the rock being drilled, a well operator may adjust production valves and/or choke settings in order to regulate the progress of the drilling operation and also minimize wellbore kick through early kick detection. In other cases, the well operator may alter mud properties in an effort to optimize drilling efficiency or formation evaluation efficiency. Other drilling and completion parameters that may be altered by a well operator upon consideration of the data include changing a planned cementing and/or casing program and optimizing a well completion design.

In some cases, the data may reveal excessive amounts of hazardous or otherwise toxic gases being returned to the surface. Such gases may pose a potential health hazard to rig workers and the surrounding environment. In such cases, the well operator may proactively reduce the amount of hazardous/toxic gases by introducing one or more remedial additives or components to the drilling fluid.

In other cases, the data may indicate an increased amount of viable hydrocarbons in the drilled borehole, such as in a particular lateral trajectory of the wellbore. In such cases, the well operator may manipulate the well plan and/or geosteering so that the resulting wellbore is formed substantially in and through the observed hydrocarbon-rich strata or region. In other words, the planned trajectory of the well path may be manipulated or otherwise altered by geosteering the drilling equipment such that the borehole penetrates a larger portion of the hydrocarbon-rich strata than would have otherwise been penetrated.

By measuring the gas content directly in the drilling fluid, it is not necessary to extract a gas sample from the fluid for mud logging gas analysis. This may prove particularly advantageous since the gas extraction process normally used in mud logging gas analyses is not always efficient since it depends on a number of variables including temperature, flow rate, viscosity, drilling fluid type, etc. Using the optical computing devices described herein will effectively eliminate all these variables from the analysis. By reducing variation in the analysis, the accuracy of the results may greatly increase. The reliability is also improved since there are fewer moving parts. In addition, using the optical computing devices described herein dramatically reduces the lag time between drilling fluid exiting the wellhead and the measurement results being available. Update rates are also greatly improved over traditional extraction systems.

The optical computing devices can be deployed at various points within a drilling fluid circulation system to monitor the drilling fluid and its associated gas content. Depending on the location of the particular optical computing device, different types of information about the fluid can be obtained. In some cases, for example, the optical computing devices can be used to monitor the type and concentration of gases therein before and after the drilling fluid circulates into and out of a wellbore. In other cases, the optical computing devices may be used to analyze an extracted gas sample in real-time following its extraction from the drilling fluid via a traditional drilling fluid sampling process. In other cases, the optical computing devices may be used to monitor the drilling fluid at or near a wellbore choking device so as to register real-time gas concentrations of the drilling fluid while the drilling fluid circulates at wellbore conditions.

As used herein, the term "fluid" refers to any substance that is capable of flowing, including particulate solids, liquids, gases, slurries, emulsions, powders, muds, mixtures, combinations thereof, and the like. In some embodiments, the fluid is a drilling fluid or drilling "mud," including water-based drilling fluids, oil-based drilling fluids, synthetic drilling fluids, and the like. In other embodiments, the fluid may be a completion fluid or a clean-up fluid such as, but not limited to, fresh water, saltwater (e.g., water containing one or more salts dissolved therein), brine (e.g., saturated salt water, chloride salts, bromide salts, combinations thereof, etc.), seawater, a spacer fluid, base fluids, or other treatment fluids known in the art.

As used herein, the term "characteristic" refers to a chemical, mechanical, or physical property of the fluid. A characteristic of the fluid may include a quantitative value or concentration of one or more chemical constituents or compounds present within the fluid. Such chemical constituents may be referred to herein as "analytes." Illustrative characteristics of a substance that can be monitored with the optical computing devices disclosed herein can include, for example, chemical composition (e.g., identity and concentration in total or of individual components or compounds), phase presence (e.g., gas, oil, water, etc.), impurity content, pH, alkalinity, viscosity, density, ionic strength, total dissolved solids, salt content (e.g., salinity), porosity, opacity, bacterial content, total hardness, combinations thereof, state of matter (solid, liquid, gas, emulsion, mixtures, etc), and the like.

Moreover, the phrase "characteristic of interest of/in a fluid" may be used herein to refer to the concentration or characteristic of a gas contained in or otherwise entrained within the fluid. Exemplary gases that may be monitored or otherwise measured with the optical computing devices as contained within a drilling fluid, for example, include, but are not limited to, methane, ethane, propane, n-butane, n-pentane, iso-butane, iso-pentane, neo-pentane, benzene, toluene, carbon dioxide, carbon monoxide, hydrogen sulfide, acetic acid, argon, helium, oxygen, nitrogen, water, hydrogen, carbonyl sulfide, carbon disulfide, and any combination thereof.

As used herein, the term "flow path" refers to a route through which a fluid is capable of being transported between at least two points. In some cases, the flow path need not be continuous or otherwise contiguous between the two points. Exemplary flow paths include, but are not limited to, a flow line, a pipeline, production tubing, drill string, work string, casing, a wellbore, an annulus defined between a wellbore and any tubular arranged within the wellbore, a mud pit, a subterranean formation, etc., combinations thereof, or the like. It should be noted that the term "flow path" does not necessarily imply that a fluid is flowing therein, rather that a fluid is capable of being transported or otherwise flowable therethrough.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a fluid and produce an output of electromagnetic radiation from a processing element arranged within the optical computing device. The processing element may be, for example, an integrated computational element (ICE), also known as a multivariate optical element (MOE), used in the optical computing device. The electromagnetic radiation that optically interacts with the processing element is changed so as to be readable by a detector, such that an output of the detector can be correlated to a characteristic of the fluid, such as the type and concentration of a gas in the fluid. The output of electromagnetic radiation from the processing element can be reflected electromagnetic radiation, transmitted electromagnetic radiation, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements or multivariate optical elements), a fluid, or a gas present within the fluid. Accordingly, optically interacted light refers to electromagnetic radiation that has been reflected, transmitted, scattered, diffracted, or absorbed by, emitted, or re-radiated, for example, using a processing element, but may also apply to interaction with a fluid or a gas entrained within the fluid.

The exemplary systems and methods described herein will include at least one optical computing device arranged along or in a flow path in order to monitor a fluid contained therein. Each optical computing device may include an electromagnetic radiation source, at least one processing element (e.g., an integrated computational element), and at least one detector arranged to receive optically interacted light from the at least one processing element or the fluid. In some embodiments, the exemplary optical computing devices may be specifically configured for detecting, analyzing, and quantitatively measuring a particular characteristic of the fluid, such as the type and concentration of a gas present within the fluid. In other embodiments, the optical computing devices may be general purpose optical devices, with post-acquisition processing (e.g., through computer means) being used to specifically detect the characteristic of the fluid.

The presently described optical computing devices can perform calculations (analyses) in real-time or near real-time without the need for time-consuming sample processing. Moreover, the optical computing devices can be specifically configured to detect and analyze particular characteristics of a fluid or a gas present within the fluid. As a result, interfering signals are discriminated from those of interest in the fluid by appropriate configuration of the optical computing devices, such that the optical computing devices provide a rapid response regarding the characteristics of the fluid as based on the detected output. In some embodiments, the detected output can be converted into a voltage that is distinctive of the magnitude of the characteristic of the fluid.

The optical computing devices can be configured to detect not only the composition and concentrations of a gas within a fluid, but they also can be configured to determine physical properties and other characteristics of the fluid and/or the gas based on an analysis of the electromagnetic radiation received from the fluid and/or the gas. For example, the optical computing devices can be configured to determine the concentration of an analyte and correlate the determined concentration to a characteristic of the fluid. As will be appreciated, the optical computing devices may be configured to detect as many characteristics (e.g., gas compounds and their respective concentrations) of the fluid as desired. All that is required to accomplish the monitoring of multiple characteristics is the incorporation of suitable processing and detection means within the optical computing device for each characteristic. In some embodiments, the properties of the fluid can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given fluid and/or gas will be determined.

The optical computing devices described herein utilize electromagnetic radiation to perform calculations, as opposed to the hardwired circuits of conventional electronic processors. When electromagnetic radiation interacts with a fluid, unique physical and chemical information about the fluid is encoded in the electromagnetic radiation that is reflected from, transmitted through, or radiated from the fluid. This information is often referred to as the spectral "fingerprint" of the fluid. The optical computing devices described herein are capable of extracting the information of the spectral fingerprint of multiple characteristics or analytes within a fluid, and converting that information into a detectable output relating to one or more characteristics of the fluid or a gas present within the fluid. That is, through suitable configurations of the optical computing devices, electromagnetic radiation associated with a characteristic or analyte of interest of a fluid can be separated from electromagnetic radiation associated with all other components of the fluid in order to estimate the properties of the fluid in real-time or near real-time.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the fluid using a conventional spectroscopic instrument. The spectrum of interest of a given characteristic typically includes any number of different wavelengths. It should be understood that the exemplary ICE 100 in FIG. 1 does not in fact represent any particular characteristic of a given fluid, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and SiO$_2$) may vary, depending on the application, cost of materials, and/or applicability of the material to the given fluid.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest.

Figure 2:
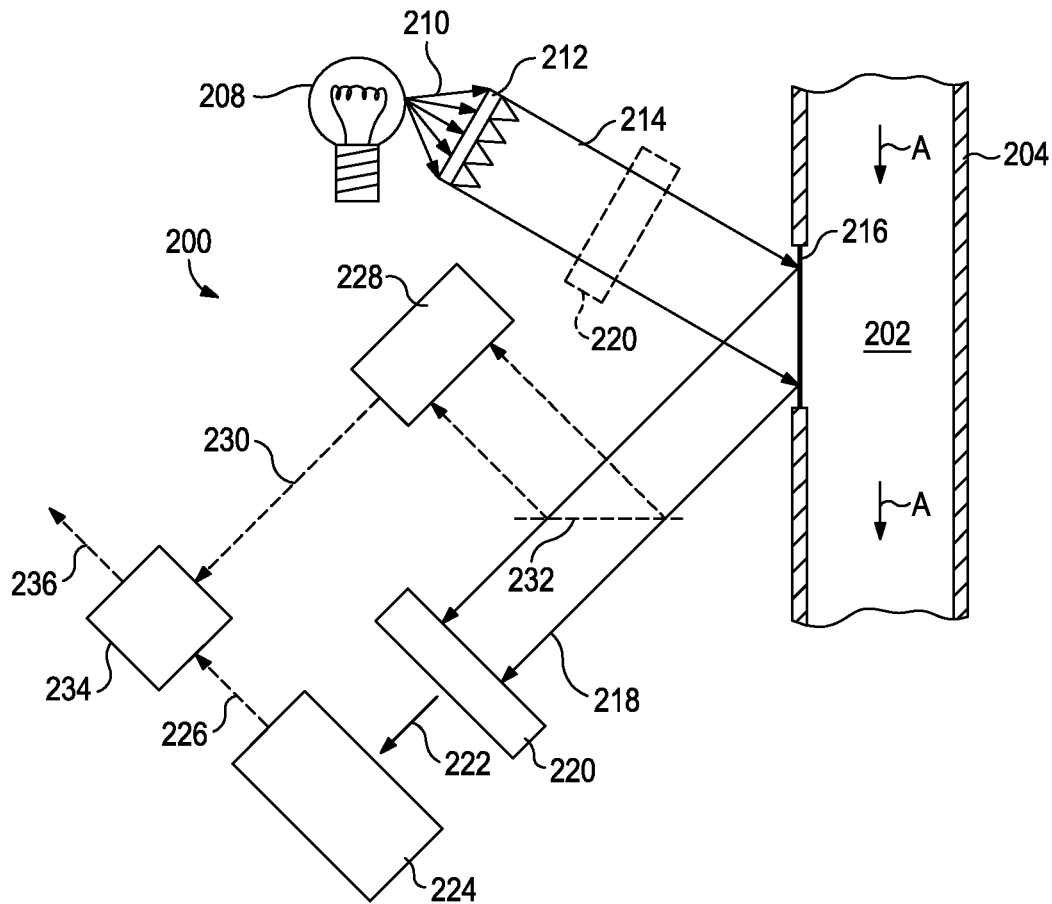
FIG. 2 illustrates an exemplary optical computing device for monitoring a fluid, according to one or more embodiments.

Referring now to FIG. 2, illustrated is an exemplary optical computing device 200 for monitoring a fluid 202, according to one or more embodiments. In the illustrated embodiment, the fluid 202 may be contained or otherwise flowing within an exemplary flow path 204. The flow path 204 may be a flow line, a pipeline, a wellbore, an annulus defined within a wellbore, or any flow lines or pipelines extending to/from a wellbore. The fluid 202 present within the flow path 204 may be flowing in the general direction indicated by the arrows A (i.e., from upstream to downstream). Portions of the flow path 204 may be arranged substantially vertical, substantially horizontal, or any directional configuration therebetween, without departing from the scope of the disclosure.

The optical computing device 200 may be configured to determine a characteristic of interest in the fluid 202, such as the type and/or concentration of a gas present within the fluid 202. In some embodiments, the device 200 may include an electromagnetic radiation source 208 configured to emit or otherwise generate electromagnetic radiation 210. The electromagnetic radiation source 208 may be any device capable of emitting or generating electromagnetic radiation, as defined herein. For example, the electromagnetic radiation source 208 may be a light bulb, a light emitting diode (LED), a laser, a blackbody, a photonic crystal, an X-Ray source, combinations thereof, or the like. In some embodiments, a lens 212 may be configured to collect or otherwise receive the electromagnetic radiation 210 and direct a beam 214 of electromagnetic radiation 210 toward the fluid 202. The lens 212 may be any type of optical device configured to transmit or otherwise convey the electromagnetic radiation 210 as desired, such as a normal lens, a Fresnel lens, a diffractive optical element, a holographic graphical element, a mirror (e.g., a focusing mirror), or a type of collimator. In other embodiments, the lens 212 may be omitted from the device 200 and the electromagnetic radiation 210 may instead be directed toward the fluid 202 directly from the electromagnetic radiation source 208.

In one or more embodiments, the device 200 may also include a sampling window 216 arranged adjacent to or otherwise in contact with the fluid 202 for detection purposes. The sampling window 216 may be made from a variety of transparent, rigid or semi-rigid materials that are configured to allow transmission of the electromagnetic radiation 210 therethrough. For example, the sampling window 216 may be made of, but is not limited to, glasses, plastics, semi-conductors, crystalline materials, polycrystalline materials, hot or cold-pressed powders, combinations thereof, or the like. After passing through the sampling window 216, the electromagnetic radiation 210 impinges upon and optically interacts with the fluid 202. As a result, optically interacted radiation 218 is generated by and reflected from the fluid 202. Those skilled in the art, however, will readily recognize that alternative variations of the device 200 may allow the optically interacted radiation 218 to be generated by being transmitted, scattered, diffracted, absorbed, emitted, or re-radiated by and/or from the fluid 202, without departing from the scope of the disclosure.

The optically interacted radiation 218 generated by the interaction with the fluid 202 may be directed to or otherwise be received by an ICE 220 arranged within the device 200. The ICE 220 may be a spectral component substantially similar to the ICE 100 described above with reference to FIG. 1. Accordingly, in operation the ICE 220 may be configured to receive the optically interacted radiation 218 and produce modified electromagnetic radiation 222 corresponding to a particular characteristic of the fluid 202. In particular, the modified electromagnetic radiation 222 is electromagnetic radiation that has optically interacted with the ICE 220, whereby an approximation of the regression vector corresponding to the characteristic of the fluid 202 is obtained.

While FIG. 2 depicts the ICE 220 as receiving reflected electromagnetic radiation from the fluid 202, the ICE 220 may be arranged at any point along the optical train of the device 200, without departing from the scope of the disclosure. For example, in one or more embodiments, the ICE 220 (as shown in dashed lines) may be arranged within the optical train prior to the sampling window 216 and equally obtain substantially the same results. In other embodiments, the ICE 220 may generate the modified electromagnetic radiation 222 through reflection, instead of transmission therethrough.

Moreover, while only one ICE 220 is shown in the device 200, embodiments are contemplated herein which include the use of at least two ICE components in the device 200 configured to cooperatively determine the characteristic of interest in the fluid 202. For example, two or more ICE may be arranged in series or parallel within the device 200 and configured to receive the optically interacted radiation 218 and thereby enhance sensitivities and detector limits of the device 200. In other embodiments, two or more ICE may be arranged on a movable assembly, such as a rotating disc or an oscillating linear array, which moves such that individual ICE components are able to be exposed to or otherwise optically interact with electromagnetic radiation for a distinct brief period of time.

The two or more ICE components in any of these embodiments may be configured to be either associated or disassociated with the characteristic of interest in the fluid 202. In other embodiments, the two or more ICE may be configured to be positively or negatively correlated with the characteristic of interest in the fluid 202.

In some embodiments, it may be desirable to monitor more than one characteristic of interest at a time using the device 200, such as detecting multiple types or compounds of gases within the fluid 202. In such embodiments, various configurations for multiple ICE components can be used, where each ICE component is configured to detect a particular and/or distinct characteristic of interest. In some embodiments, the characteristic can be analyzed sequentially using multiple ICE components that are provided a single beam of electromagnetic radiation being reflected from or transmitted through the fluid 202. In some embodiments, multiple ICE components can be arranged on a rotating disc, where the individual ICE components are only exposed to the beam of electromagnetic radiation for a short time. Advantages of this approach can include the ability to analyze multiple characteristics of the fluid 202 using a single optical computing device 200 and the opportunity to assay additional characteristics (e.g., types or compounds of gases within the fluid 202) simply by adding additional ICE components to the rotating disc.

In other embodiments, multiple optical computing devices can be placed at a single location along the flow path 204, where each optical computing device contains a unique ICE that is configured to detect a particular characteristic of interest in the fluid 202. In such embodiments, a beam splitter can divert a portion of the electromagnetic radiation being reflected by, emitted from, or transmitted through the fluid 202 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 204. Likewise, multiple detection stations, each containing optical computing devices in parallel, can be placed in series for performing a similar analysis.

The modified electromagnetic radiation 222 generated by the ICE 220 may subsequently be conveyed to a detector 224 for quantification of the signal. The detector 224 may be any device capable of detecting electromagnetic radiation, and may be generally characterized as an optical transducer. In some embodiments, the detector 224 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 224 may be configured to produce an output signal 226 in real-time or near real-time in the form of a voltage (or current) that corresponds to the particular characteristic of interest in the fluid 202. The voltage returned by the detector 224 is essentially the dot product of the optical interaction of the optically interacted radiation 218 with the respective ICE 220 as a function of the concentration of the characteristic of interest of the fluid 202. As such, the output signal 226 produced by the detector 224 and the concentration of the characteristic may be related, for example, directly proportional. In other embodiments, however, the relationship may correspond to a polynomial function, an exponential function, a logarithmic function, and/or a combination thereof.

In some embodiments, the device 200 may include a second detector 228, which may be similar to the first detector 224 in that it may be any device capable of detecting electromagnetic radiation. The second detector 228 may be used to detect radiating deviations stemming from the electromagnetic radiation source 208. Undesirable radiating deviations can occur in the intensity of the electromagnetic radiation 210 due to a wide variety of reasons and potentially causing various negative effects on the device 200. These negative effects can be particularly detrimental for measurements taken over a period of time. In some embodiments, radiating deviations can occur as a result of a build-up of film or material on the sampling window 216 which has the effect of reducing the amount and quality of light ultimately reaching the first detector 224. Without proper compensation, such radiating deviations could result in false readings and the output signal 226 would no longer be primarily or accurately related to the characteristic of interest.

To compensate for these types of undesirable effects, the second detector 228 may be configured to generate a compensating signal 230 generally indicative of the radiating deviations of the electromagnetic radiation source 208, and thereby normalize the output signal 226 generated by the first detector 224. As illustrated, the second detector 228 may be configured to receive a portion of the optically interacted radiation 218 via a beamsplitter 232 in order to detect the radiating deviations. In other embodiments, however, the second detector 228 may be arranged to receive electromagnetic radiation from any portion of the optical train in the device 200 in order to detect the radiating deviations, without departing from the scope of the disclosure.

In some applications, the output signal 226 and the compensating signal 230 may be conveyed to or otherwise received by a signal processor 234 communicably coupled to both the detectors 224, 228. The signal processor 234 may be a computer including a processor and a machine-readable storage medium having instructions stored thereon, which, when executed by the processor 234, cause the optical computing device 200 to perform a number of operations, such as determining a characteristic of interest of the fluid 202. For instance, the concentration of each characteristic detected with the optical computing device 200 can be fed into an algorithm operated by the signal processor 234. The algorithm can be part of an artificial neural network configured to use the concentration of each detected characteristic in order to evaluate the overall characteristic(s) or quality of the fluid 202.

The signal processor 234 may also be configured to computationally combine the compensating signal 230 with the output signal 226 in order to normalize the output signal 226 in view of any radiating deviations detected by the second detector 228. Computationally combining the output and compensating signals 226, 230 may entail computing a ratio of the two signals 226, 230. For example, the concentration or magnitude of each characteristic determined using the optical computing device 200 can be fed into an algorithm run by the signal processor 234. The algorithm may be configured to make predictions on how the characteristics of the fluid 202 change if the concentrations of one or more components or additives are changed relative to one another.

In real-time or near real-time, the signal processor 234 may be configured to provide a resulting output signal 236 corresponding to the characteristic of interest in the fluid 202, such as the concentration of a gas present in the fluid 202. The resulting output signal 236 may be readable by an operator who can consider the results and make proper adjustments or take appropriate action, if needed. In some embodiments, the resulting signal output 236 may be conveyed, either wired or wirelessly, to an operator for consideration. In other embodiments, the resulting output signal 236 may be recognized by the signal processor 234 as being within or without a predetermined or preprogrammed range of suitable operation and may alert the operator of an out of range reading so appropriate corrective action may be taken, or otherwise autonomously undertake the appropriate corrective action such that the resulting output signal 236 returns to a value within the predetermined or preprogrammed range of suitable operation.

Figure 3:
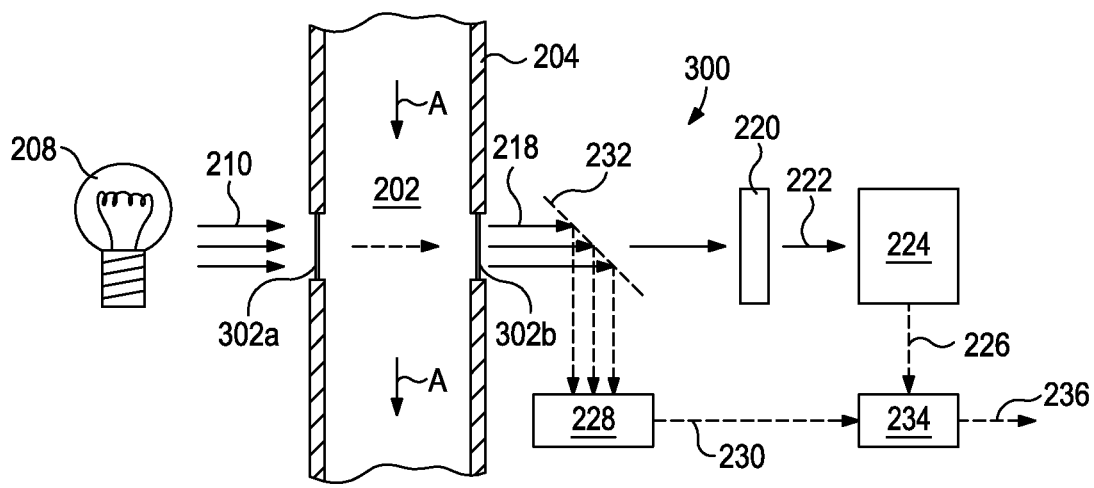
FIG. 3 illustrates another exemplary optical computing device for monitoring a fluid, according to one or more embodiments.

Referring now to FIG. 3, illustrated is another exemplary optical computing device 300 for monitoring the fluid 202, according to one or more embodiments. The optical computing device 300 may be similar in some respects to the optical computing device 200 of FIG. 2, and therefore may be best understood with reference thereto where like numerals indicate like elements that will not be described again. Again, the optical computing device 300 may be configured to determine the concentration of a characteristic of interest in the fluid 202, such as the concentration of a gas within the fluid 202, as contained within the flow path 204. Unlike the device 200 of FIG. 2, however, the optical computing device 300 in FIG. 3 may be configured to transmit the electromagnetic radiation 210 through the fluid 202 via a first sampling window 302a and a second sampling window 302b arranged radially-opposite the first sampling window 302a on the flow path 204. The first and second sampling windows 302a,b may be similar to the sampling window 216 described above in FIG. 2 and therefore will not be described again.

As the electromagnetic radiation 210 passes through the fluid 202 via the first and second sampling windows 302a,b, it optically interacts with the fluid 202 and optically interacted radiation 218 is subsequently directed to or otherwise received by the ICE 220 as arranged within the device 300. It is again noted that, while FIG. 3 depicts the ICE 220 as receiving the optically interacted radiation 218 as transmitted through the sampling windows 302a,b, the ICE 220 may equally be arranged at any point along the optical train of the device 300, without departing from the scope of the disclosure. For example, in one or more embodiments, the ICE 220 may be arranged within the optical train prior to the first sampling window 302a and equally obtain substantially the same results. In yet other embodiments, the ICE 220 may generate the modified electromagnetic radiation 222 through reflection, instead of transmission therethrough. Moreover, as with the device 200 of FIG. 2, embodiments are contemplated herein which include the use of at least two ICE components in the device 300 configured to cooperatively determine the characteristic of interest in the fluid 202.

The modified electromagnetic radiation 222 generated by the ICE 220 is subsequently conveyed to the detector 224 for quantification of the signal and generation of the output signal 226 which corresponds to the particular characteristic of interest in the fluid 202. The device 300 may also include the second detector 228 for detecting radiating deviations stemming from the electromagnetic radiation source 208. As illustrated, the second detector 228 may be configured to receive a portion of the optically interacted radiation 218 via the beamsplitter 232 in order to detect the radiating deviations. The output signal 226 and the compensating signal 230 may then be conveyed to or otherwise received by the signal processor 234 which may computationally combine the two signals 230, 226 and provide in real-time or near real-time the resulting output signal 236 corresponding to the concentration of the characteristic of interest in the fluid 202.

Figure 4:
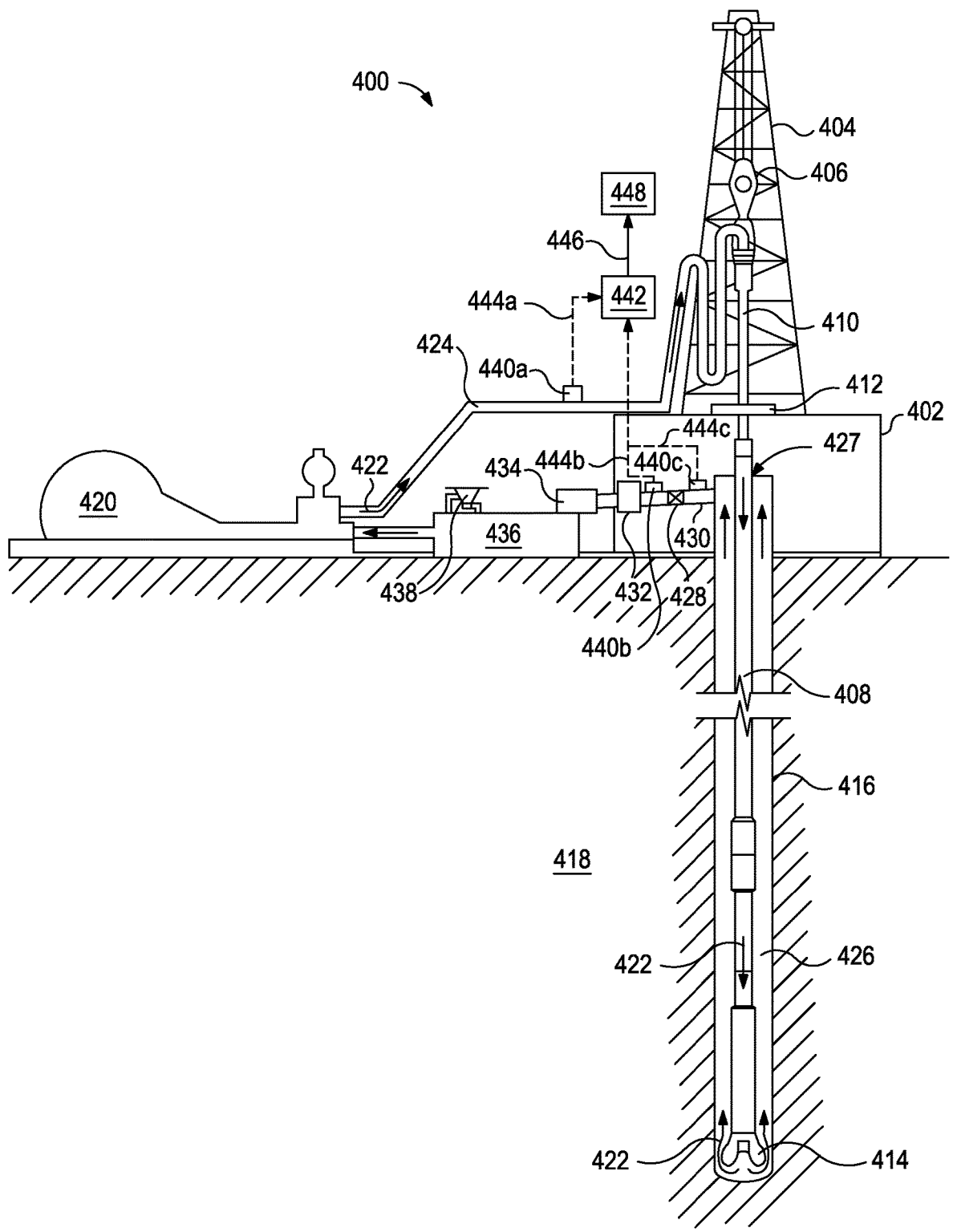
FIG. 4 illustrates an exemplary wellbore drilling assembly that may employ one or more optical computing devices for monitoring a fluid, according to one or more embodiments.

Those skilled in the art will readily appreciate the various and numerous applications that the optical computing devices 200, 300, and various alternative configurations thereof, may be suitably used with. For example, referring now to FIG. 4, illustrated is an exemplary wellbore drilling assembly 400 that may employ one or more optical computing devices as described herein in order to monitor a drilling fluid or a completion fluid, according to one or more embodiments. The drilling assembly 400 may include a drilling platform 402 that supports a derrick 404 having a traveling block 406 for raising and lowering a drill string 408. A kelly 410 supports the drill string 408 as it is lowered through a rotary table 412. A drill bit 414 is attached to the distal end of the drill string 408 and is driven either by a downhole motor and/or via rotation of the drill string 408 from the well surface. As the bit 414 rotates, it creates a borehole 416 that penetrates various subterranean formations 418.

A pump 420 (e.g., a mud pump) circulates drilling fluid 422 through a feed pipe 424 and to the kelly 410, which conveys the drilling fluid 422 downhole through an interior conduit defined in the drill string 408 and through one or more orifices in the drill bit 414. The drilling fluid 422 is then circulated back to the surface via an annulus 426 defined between the drill string 408 and the walls of the borehole 416. The drilling fluid 422 provides hydrostatic pressure to prevent formation fluids from entering into the borehole 416 and keeps the drill bit 414 cool and clean during drilling. The drilling fluid 422 also serves to carry drill cuttings and solids out of the borehole 416 and suspend the drill cuttings and solids while drilling is paused and/or when the drill bit 414 is brought in and out of the borehole 416.

As the spent drilling fluid 422 returns to the surface, it may exit the annulus 426 at the wellhead 427 and subsequently pass through one or more chokes or choke valves 428 (one shown) via an interconnecting flow line 430. The choke valve 428 may be used to maintain or otherwise regulate the pressure on the annulus 426 at surface, for example in the range of about 100 psi to about 1500 psi. As a result, this will enable drilling to continue underbalanced and is useful in reducing formation 418 damage to the reservoir, but also to facilitate increases in drilling speed. It will be appreciated, however, that the choke valve(s) 428 may be omitted in other embodiments and the spent drilling fluid 422 may instead return to the surface at atmospheric pressures, without departing from the scope of the disclosure.

Following the choke valve 428, the spent drilling fluid 422 may be conveyed to one or more drilling fluid rehabilitation devices via the interconnecting flow line 430. Such drilling fluid rehabilitation devices may include, but are not limited to, one or more degassing units 432 and solids control equipment 434. The degassing unit 432 may be any device or machine configured to separate from the drilling fluid 422 any gases (i.e., hydrocarbon and non-hydrocarbon gas species) that may have been entrained in the drilling fluid 422 while circulating in and out of the borehole 416. The solids control equipment 434 may be configured to substantially remove the drill cuttings and solids from the drilling fluid 422 and deposit a "cleaned" drilling fluid 422 into a nearby retention pit 436 (i.e., a mud pit).

Several additives or components may be added to the drilling fluid 422 in order to maintain the drilling fluid 422 in proper working order and otherwise enhance drilling capabilities. In some embodiments, the additives and components may be added to the drilling fluid 422 via a mixing hopper 438 fluidly coupled to the retention pit 436. Exemplary components that may be added to the drilling fluid 422 include, but are not limited to, emulsions, weighting materials, viscosifiers, thickeners, rheology modifiers, thinners, deflocculants, anionic polyelectrolytes (e.g., acrylates, polyphosphates, lignosulfonates, tannic acid derivates, etc.), high-heat polymers, clay stabilizers, clay inhibitors, tar treatments, water and other base fluids, combinations thereof, and the like. The rehabilitated drilling fluid 422 may then be recirculated and pumped back into the borehole 416 with the pump 420 via the feed pipe 424.

According to the present disclosure, mud logging gas analysis of the drilling fluid 422 may be undertaken by arranging one or more optical computing devices 440 (shown as optical computing devices 440a, 440b, and 440c) at various predetermined monitoring locations throughout the circulation system of the drilling assembly 400. The optical computing devices 440a-c may be substantially similar to at least one of the optical computing devices 200, 300 of FIGS. 2 and 3, respectively, and therefore will not be described again in detail. In exemplary operation, the optical computing devices 440a-c may be configured to measure and report real-time characteristics of the drilling fluid 422, such as the type and/or concentration of one or more gases present therein at their respective monitoring locations.

In one or more embodiments, the optical computing devices 440a-c may be communicably coupled to a signal processor 442 and configured to convey corresponding output signals 444a-c, respectively, to the signal processor 442. The signal processor 442 may be similar to the signal processor 234 of FIGS. 2 and 3 and may be configured to receive and process the output signals 444a-c. In particular, the signal processor 442 may employ an algorithm configured to calculate or otherwise determine the concentration or type of a gas detected at each monitoring location. The signal processor 442 may further be configured to determine the differences between any two or more of the output signals 440a-c. In other words, the signal processor 442 may be configured to determine how the concentration of the gas and/or the magnitude of the characteristic of interest in the fluid 422 changed between each monitoring location.

In real-time or near real-time, the signal processor 442 may be configured to provide a resulting output signal 446 corresponding to one or more characteristics of the fluid 422. The resulting output signal 446 may provide a measured gas content and/or the magnitude of the characteristic of interest in the fluid 422 at the various monitoring locations throughout the circulation system. In some embodiments, the resulting output signal 446 may be conveyed, either wired or wirelessly, to one or more peripheral devices 448 communicably coupled to the signal processor 442. The peripheral devices 448 may include, but are not limited to, a mobile device, computer monitor, or a printer coupled to a computer. In some embodiments, as discussed in more detail below with reference to FIGS. 5A-5D, the peripheral devices 448 may be configured to provide one or more graphical outputs such as a Pixler plot, a Haworth Plot, or a gas-ratio plot, depicting various properties, parameters, and characteristic(s) detected in the fluid 422. A well operator may then be able to consult and interpret the graphical output and thereby make intelligent decisions on how best to manage the well in response thereto.

In other embodiments, the peripheral devices 448 may include an audible or visual alarm mechanism or device that may be triggered. For example, the one or more of the output signals 444a-c may be recognized by the signal processor 442 as being within or without a predetermined or preprogrammed range of suitable operation for the drilling fluid 422. If the output signals 444a-c exceed the predetermined or preprogrammed range of operation, the resulting output signal 446 may trigger an alarm forming part of the peripheral device 448 and the alarm may be configured to alert the operator so appropriate corrective action may be taken on the drilling fluid 422. In some embodiments, the signal processor 442 may be configured to autonomously undertake the appropriate corrective action such that the resulting output signal 446 returns to a value within the predetermined or preprogrammed range of suitable operation. For example, the signal processor 442 may be communicably coupled to an automated control system (not shown) that may be configured to undertake the required corrective action.

Referring now to FIGS. 5A-5D, with continued reference to FIG. 4, illustrated are graphical depictions of signals representing measurement of gas content within zones of a subterranean formation, according to one or more embodiments. In one embodiment, the measurements may be taken by one or more of the optical computing devices 440a-c of FIG. 4, thereby rendering an output signal 446 to a peripheral device 448, such as a monitor or printer (FIG. 4). Further, the peripheral device 448 may display the output signal 446 in the form of graphical outputs such as a Pixler plots, Haworth plots, and gas ratio plots.

Figure 5A:
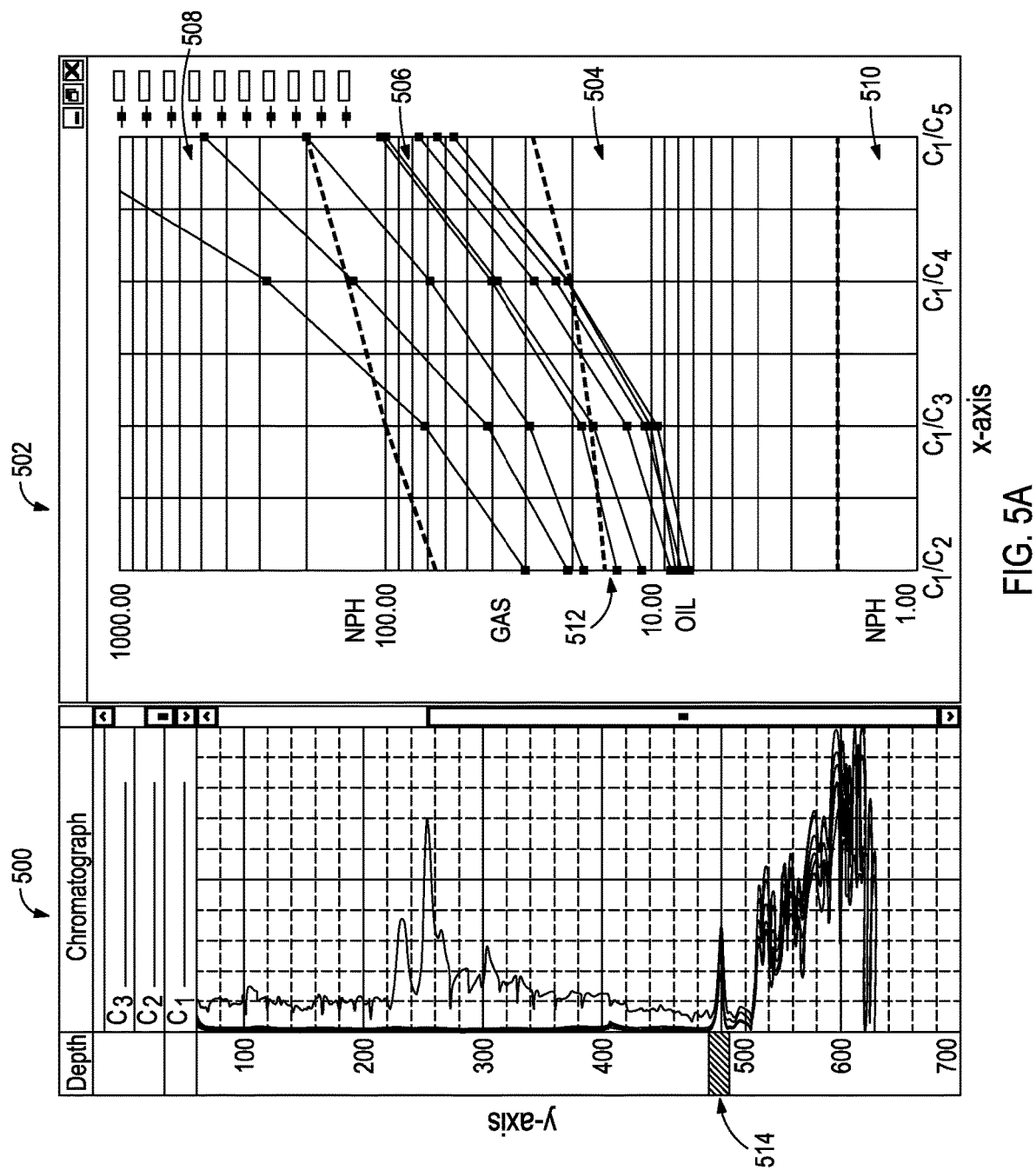
FIGS. 5A-5D illustrate exemplary graphical outputs resulting from measurement of gas content, according to one or more embodiments.
Figure 5B:
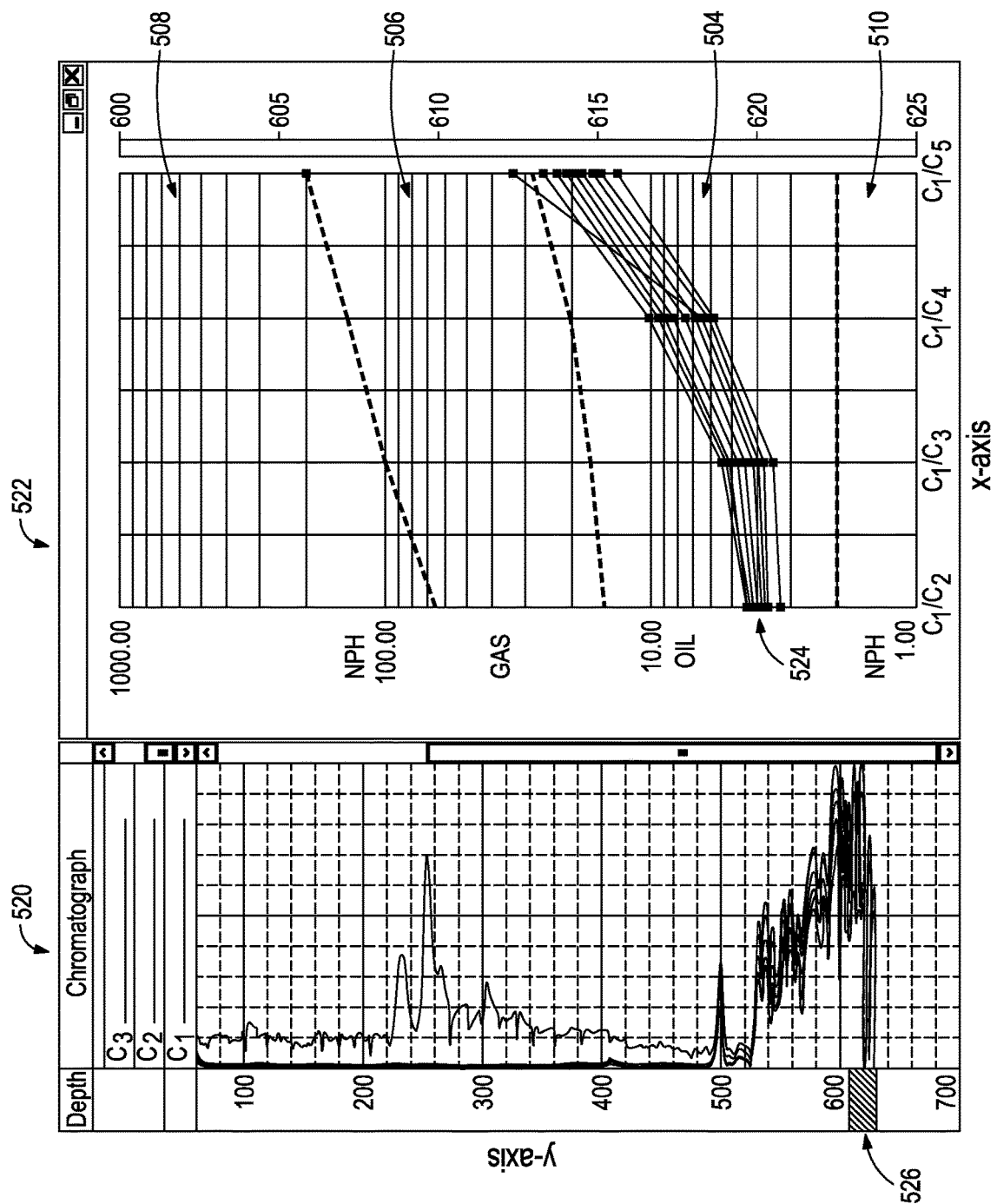

FIGS. 5A and 5B graphically depict measured gas content of a formation in the form of "Pixler" plots. Briefly, a Pixler plot is a visualization format that depicts gas ratios at varying depths of a formation, thus indicating possibilities of oil, gas, or non-productivity at the associated depth. In some cases, a Pixler plot may indicate ratios of the quantitative amounts of methane ($C_1$), ethane ($C_2$), propane ($C_3$), butane ($C_4$), and pentane ($C_5$), as displayed in the graph 502 (FIG. 5A) on the X-axis as $C_1/C_2$, $C_1/C_3$, $C_1/C_4$, and $C_1/C_5$. Generally, a ratio of $C_1/C_2$ between 2 and 15 indicates oil, a ratio of $C_1/C_2$ between 15 and 65 indicates gas, and a ratio of $C_1/C_2$ below 2 or above 65 indicates the zone is non-productive. The ratios for $C_1/C_3$, $C_1/C_4$, and $C_1/C_5$ similarly have ranges indicating zones of oil, gas, and non-productivity that are known or may be calculated by one of skill in the art.

In FIG. 5A, graph 500 depicts an overall illustration of gas measurements taken while drilling through a portion of the formation (e.g., the formation 418 of FIG. 4), thereby correlating downhole depth and gas measurements (chromatograph). Graphs 520, 540, and 560 of FIGS. 5B, 5C, and 5D, respectively, also depict depth and chromatograph information, and thus may be best understood with reference to the discussion of graph 500. As illustrated, the graph 500 depicts gas measurements at a depth ranging from approximately 100 meters to approximately 700 meters. The graph 500 illustrates that certain gases are readily present in portions of the formation, such as from about 100 meters to about 500 meters, while gases of interest are generally not present in that range. However, continuing further downhole within the formation, such as from approximately 500 meters to approximately 650 meters, certain gases of interest become readily present and the ratio of gases correspondingly changes.

The graph 502 illustrates a gas ratio Pixler plot corresponding to the gases found in depth range 514 of the graph 500. The ratio of certain gases may be used to estimate at what depth a formation may be capable of oil or gas production or both oil and gas. In the graph 502, range 504 depicts a depth range where gas ratios indicate that the formation is likely capable of oil production, range 506 corresponds to gas ratios indicating that the formation 418 is likely capable of gas production, and ranges 508 and 510 depict ranges indicating non-producing hydrocarbons. Notably, range 510 may be deemed "non-producing," even though a gas ratio falling with range 510 may indicate that the formation is capable of some oil production. The range 510 may be considered non-producing possibly due to the oil being a heavier oil which is more difficult to produce, thus the quantity of oil produced would not fall within the requirements for a "producing" well. The Y-axis of the graph 502 may be scaled logarithmically or by any other scale helpful in determining production capabilities. As gas plots 512 fall within ranges 504, 506, and 508 of the graph 502, the formation 418 may be capable of oil, gas, or nonproduction at the associated downhole depth. Therefore, a well operator may infer from the gas plots 512 that this depth is a gas cap to the reservoir.

Referring now to FIG. 5B, illustrated are graph 520 and Pixler plot graph 522. The graphs 520 and 522 are substantially similar to the graphs 500 and 502 of FIG. 5A, and therefore may be best understood with reference thereto. The gas plots 524 of the graph 522 correlate to gas measurements taken at depth 526 of the graph 520, ranging from approximately 600 meters to 625 meters downhole. As the gas plots 524 fall substantially within the oil range 504 of the graph 522, this indicates to a well operator that the formation 418 would likely be oil producing at those depths.

Figure 5C:
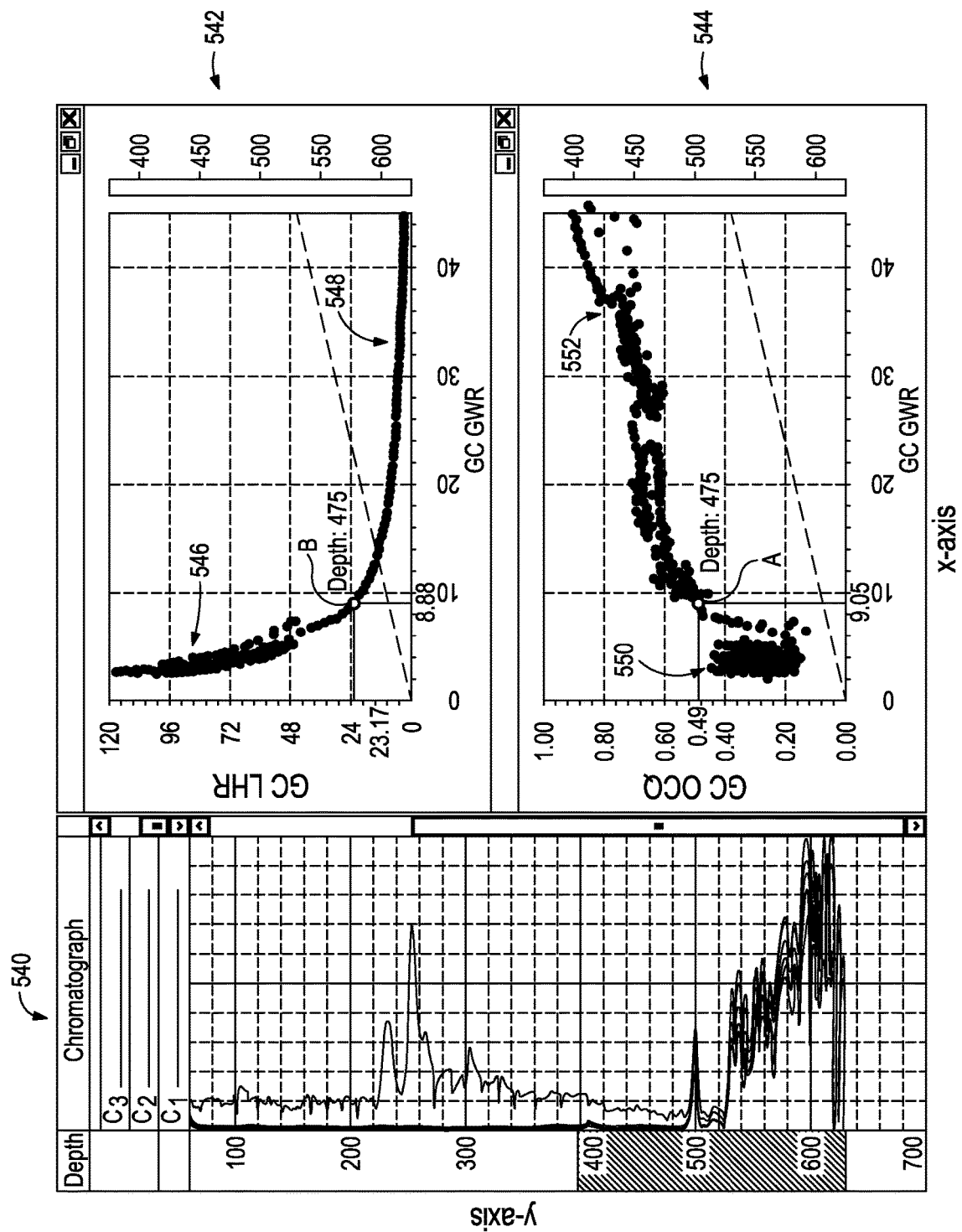

Referring now to FIG. 5C, in another embodiment, one or more "Haworth" plots may be used to illustrate ratios of measured gas, as depicted by graphs 542 and 544. Similar to the Pixler plots described above, Haworth plots depict gas ratios that may give the well operator an indication of what zone in a formation may be capable of efficient hydrocarbon production. Briefly, Haworth plots may consist of utilizing multiple graphs to indicate whether the formation of interest is capable of production at certain depths. A first graph may plot a "gas wetness ratio" (GWR) against a "light to heavy ratio" (LHR), for example, as illustrated by the graph 542. In some embodiments, the GWR may be calculated by the equation $(((C_2+C_3+C_4+C_5)/(C_1+C_2+C_3+C_4+C_5))\times 100)$, wherein $C_1$-$C_5$ represent the gases previously discussed. A GWR value of less than 0.5 may represent non-potential for dry gas, a GWR value of 0.5 to 17.5 may indicate a potential for gas, a GWR value of 17.5 to 40 may indicate a potential for oil, and a GWR value greater than 40 may indicate a potential for residual oil. The LHR may be calculated by the equation $((C_1+C_2)/(C_3+C_4+C_5))$, wherein the ratio may show a decreasing trend with increasing fluid density.

The graph 540 is substantially similar to graphs 500 and 520 of FIGS. 5A and 5B, respectively, and thus may be best understood with reference thereto and will therefore not be discussed. The graph 542 illustrates a plot of GWR against LHR for gases indicated in graph 540 within a depth range of approximately 400 meters to approximately 625 meters downhole. The graph 542 illustrates that calculations of GWR and LHR for gases at shallow depths of the formation result in high LHR values and low GWR values (e.g., plot location 546). As downhole depth increases, GWR value increases and LHR value decreases, for example, the downhole depth of 625 having a high GWR and low LHR (e.g., plot location 548). A GWR value falling within the range of 0.5 to 17.5 indicates a likely presence of gas. Accordingly, the graph 542 indicates to a well operator that the formation is gas producing from approximately 400 meters to 550 meters downhole. Further, a GWR value falling within the range of 17.5 to 40 indicates a likely presence of oil. Accordingly, the graph 542 indicates that the formation is likely gas producing from approximately 550 meters to 625 meters downhole. However, for a more accurate determination of where the transition from gas to oil may occur, the Haworth analysis includes implementation of a second set of calculations and graph.

The second graph utilized in a Haworth analysis plots GWR against an "oil character qualifier" (OCQ), as depicted in graph 544. The OCQ may be calculated by the equation $((C_4+C_5)/C_3)$. Accordingly, the graph 544 illustrates that calculations for gases at shallow depths results in a cluster around plot location 550. As downhole depth increases, calculations result in increasing GWR and OCQ values, indicated by plot location 552. The critical junction may be where OCQ is a value of 0.5. Where the OCQ is less than 0.5, gas potential is indicated. Where the OCQ is greater than 0.5, gas, light oil, or condensate is indicated. Upon finding where OCQ of 0.5 intersects the gas plot, such as at location A of the graph 544, the GWR value should be noted. This value may then be correlated back to the first graph, as seen at location B of the graph 542. Upon performing such analysis, a well operator is more accurately informed that a transition from gas to oil does not occur at the previously estimated 550 meters downhole, but occurs at a shallower depth of approximately 475 meters downhole.

Figure 5D:
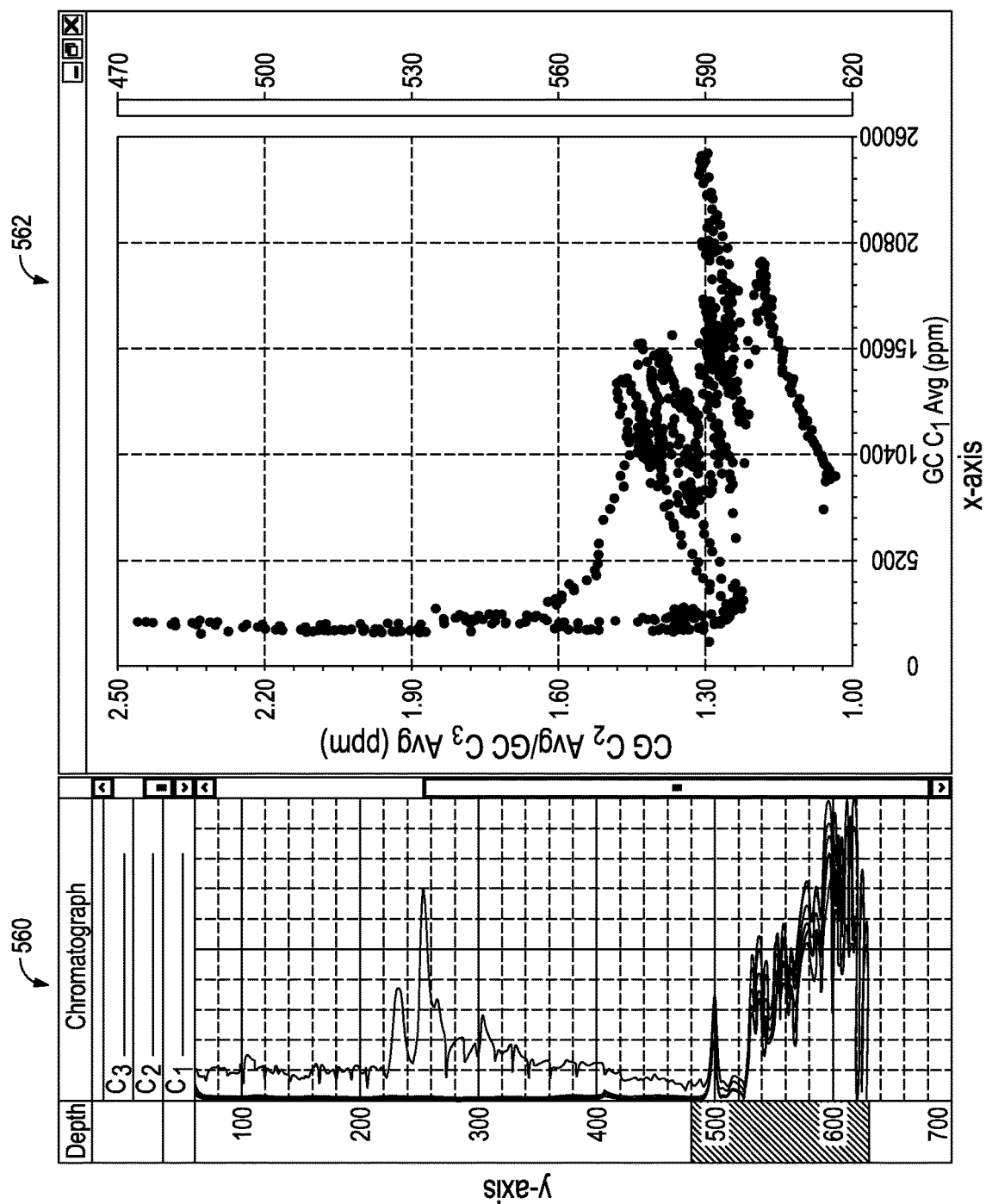

Referring now to FIG. 5D, illustrated is another exemplary gas ratio plot, according to one or more embodiments. FIG. 5D provides graphs 560 and 562, where graph 560 is substantially similar to the graphs 540, 520, and 500, and thus can be best understood with respect thereto and will not be further discussed. The graph 562, however, illustrates a plot where the Y-axis indicates a calculation of average $C_2$ values divided by average $C_3$ values and the X-axis indicates a calculation of $C_1$ values. As shown on the graph 560, and the legend of the graph 562, data is illustrated for a depth range of approximately 470 to 620 meters downhole. In one embodiment, examination of the gas ratio plot of graph 562 may prove advantageous in helping a well operator differentiate fluid properties against depth in reservoir zones of interest.

One of skill in the art will appreciate that the graphs depicted and described with reference to FIGS. 5A-5D are merely exemplary embodiments of illustrations depicting gas measurements of a formation, thus not limiting the scope of the present disclosure.

Referring again to FIG. 4, as illustrated, a first optical computing device 440a may be arranged to monitor the drilling fluid 422 as it is being introduced into the borehole 416 and a second optical computing device 440b may be arranged to monitor the drilling fluid 422 after it has returned to the surface and is otherwise de-pressurized via the choke valve 428. More particularly, the first optical computing device 440a may be arranged in the feed pipe 424 leading to the derrick 404 from the pump 420 (or otherwise at any fluidly communicable location following the pump 420 and before the borehole 416), and the second optical computing device 440b may be arranged on or otherwise coupled to the flow line 430 before the degassing unit 432 (e.g., adjacent an inlet to the degassing unit 432). As will be appreciated, more than one optical computing device may be arranged at each of these monitoring locations, without departing from the scope of the disclosure.

The first output signal 444a may be indicative of the type/concentration of a gas in the drilling fluid 422 or another characteristic of the fluid 422 as the drilling fluid 422 enters the borehole 416. Likewise, the second output signal 444b may be indicative of the type/concentration of the gas or another characteristic of the fluid 422 as the drilling fluid 422 exits the borehole 416 de-pressurized. The signal processor 442 may receive the output signals 444a,b in real-time and provide the resulting output signal 446 that may be considered by an operator via the one or more peripheral devices 448, as described above. In some embodiments, the resulting output signal 446 may inform the operator of the type/concentration of gas in the drilling fluid 422 as the drilling fluid 422 enters the borehole 416, as per the first output signal 444a. In other embodiments, the resulting output signal 446 may inform the operator of the type/concentration of the gas in the drilling fluid 422 as the drilling fluid 422 exits the borehole 416, as per the second output signal 444b. As a result, the operator may be able to conduct mud logging gas analyses of the drilling fluid 422 without having to extract a gas sample from the returning drilling fluid 422.

In yet other embodiments, the signal processor 442 may be configured to make a comparison between the first and second output signals 444a,b, and thereby provide the operator with a resulting output signal 446 via the peripheral devices 448 that details the differences between the two output signals 444a,b. As such, the operator may be apprised as to the quantity and concentration of one or more gases that may have entered or otherwise become entrained in the drilling fluid 422 while circulating through the borehole 416. Such data may be useful in providing information as to the hydrocarbon content of the rock being drilled through and, as a result, the operator may decide to adjust one or more drilling or completion parameters in response thereto.

For example, in some embodiments, the resulting output signal 446 may inform the operator that a particular type or quantity of favorable gas is found in a particular strata or region of the subterranean formation 418 while drilling. As a result, at least one drilling parameter may be adjusted in response thereto, such as altering the geosteering of the drill bit 414 so that the borehole 416 may be drilled or formed substantially in that strata or zone. In some embodiments, the favorable gas may be one or more hydrocarbons that may be produced for processing. In other embodiments, however, the favorable gas may be helium. Those skilled in the art will readily recognize that an increased amount of helium returning to the surface as entrained in the drilling fluid 422 may be an indication of high porosity in the formation 418, and high porosity can signify a zone capable of increased production rates. When such gases and hydrocarbons are detected, the operator may alter the geosteering well path such that the borehole remains substantially in that stratum, thereby maximizing potential hydrocarbon production and efficiencies.

As will be appreciated, this may prove especially advantageous in deviated or horizontal wells where altering the geosteering may have the effect of maintaining the well path substantially parallel and otherwise within a hydrocarbon-bearing stratum or region. This may also prove advantageous, however, in vertical wells where the well operator may be able to log the area of the vertical borehole 416 where a high gas content is detected. At a later time, the operator may choose to return to that location and complete the borehole 416 at that location such that the hydrocarbons residing in the formation 418 at that location may be effectively produced with greater efficiency. Accordingly, the well completion design may be optimized in response to resulting output signal 446 and what is provided via the peripheral devices 448. Some well completion designs that may be altered include, but are not limited to, changing a cementing program, changing a casing program or design, or optimizing placement of downhole perforations, sliding sleeves, and slotted liners. Optimizations resulting from such well completion alterations may include containment of unwanted fluids downhole, such as water or unwanted gas, and may also include optimizing isolation of zones from which production is not required. Further, nearby wells having similar (correlated) output signals 444a-c or output signal 446 may implement similar optimizations.

In some embodiments, the resulting output signal 446 may also be configured to inform an operator via the peripheral devices 448 of hazardous, corrosive, or otherwise toxic gases that may be entrained in the drilling fluid 422. Hazardous, corrosive, and/or toxic gases, such as hydrogen sulfide ($H_2S$) and the like, may pose a danger to rig operators and the surrounding environment. In at least one embodiment, for example, the second output signal 444b of the second optical computing device 440b may provide the real-time concentration of hydrogen sulfide ($H_2S$) entrained in the drilling fluid 422 as it returns to the surface. If the registered level of $H_2S$ surpasses a predetermined "safe" limit, the signal processor 442 may be configured to trigger an alarm by sending the resulting output signal 446 to the peripheral devices 448 indicating the same. In response to the alarm, the operator may act by shutting down the well or adding $H_2S$ scavengers or other additives to the drilling fluid 422 via the hopper 438 to remedy the situation.

In some embodiments, the hazardous, corrosive, or otherwise toxic gas may be methane as entrained in the drilling fluid 422. Since methane is highly explosive, increased amounts of the gas in the returning drilling fluid 422 may pose a substantial risk to rig operators and the surrounding environment. Accordingly, if there is an excessive amount of methane being detected by, for example, the second optical computing device 440b, such that it surpasses a predetermined "safe" limit, the signal processor 442 may be configured to trigger an alarm via the resulting output signal 446 and the peripheral devices 448. In response to the alarm, the operator may act to remedy the situation. For example, the operator may "shut in" the well using blow-out preventers or the like and then extract the methane in a controlled manner using choke and kill lines associated with the blow-out preventers.

In some embodiments, the drilling fluid 422 returned to the surface may be monitored using the third optical computing device 440c prior to full de-pressurization. As illustrated, the third optical computing device 440c may be arranged in fluid communication with the interconnecting flow line 430 following the wellhead 427 and otherwise arranged prior to the choke valve 428. Similar to the second optical computing device 440b, the third optical computing device 440c may be configured to monitor the drilling fluid 422 after its return to the surface for gases (both hydrocarbon and non-hydrocarbon gas species) that may have become entrained therein after having circulated through the borehole 416. When the drilling fluid 422 exits the choke valve 428, any gases entrained therein will immediately break out or otherwise precipitate out of the drilling fluid 422. Accordingly, the third optical computing device 440c may be advantageous in providing a real or near real-time concentration of one or more gases in the drilling fluid 422 as it circulates at or near actual downhole drilling environment conditions. The output signal 444c from the third optical computing device 440c, therefore, may be useful in mud logging gas analysis of the drilling fluid 422 at downhole operating conditions.

Similar to the second optical computing device 440b, the third optical computing device 440c may be configured to detect and report increased amounts of a favorable gas in the borehole 416. The resulting output signal 446 may then inform the operator where a particular type or quantity of favorable gas is found in the borehole 416 and, as a result, at least one drilling parameter may be adjusted in response thereto. For example, the operator may alter the geosteering of the drill bit 414 so that the borehole 416 may be drilled or formed substantially in that stratum or zone. In vertical boreholes 416, the well operator may be able to log the area of the borehole 416 where a high gas content is detected and, at a later time, return to that location and complete the borehole 416 at that location such that the hydrocarbons residing in the formation 418 at that location may be effectively produced with greater efficiency.

The third optical computing device 440c may also be configured to detect hazardous, corrosive, or otherwise toxic gases (i.e., $H_2S$, methane, etc.) that may be entrained in the drilling fluid 422. The resulting output signal 446 in such cases may inform an operator via the peripheral devices 448 of the presence of such gases, and the operator may then act to remedy the situation. In other embodiments, the signal processor 442 may autonomously act to remedy the situation, such as by shutting down the well or adding $H_2S$ scavengers or other additives to the drilling fluid 422 via the hopper 438 to remedy the situation. For example, as briefly mentioned above, the signal processor 442 may be communicably coupled to an automated control system (not shown) that may be configured to undertake the required corrective action.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments disclosed herein include:

A. A system that may include a flow path circulating a drilling fluid into and out of a borehole during drilling operations, a first optical computing device arranged near an outlet of the borehole and having a first integrated computational element configured to optically interact with the drilling fluid near the outlet of the borehole and generate a first output signal corresponding to a concentration of a gas present in the drilling fluid at the outlet, a signal processor communicably coupled to the first optical computing device and configured to receive the first output signal and determine the concentration of the gas present in the drilling fluid at the outlet of the borehole, thereby resulting in a resulting output signal being generated by the signal processor, and one or more peripheral devices communicably coupled to the signal processor and configured to receive the resulting output signal and report the resulting output signal to a well operator, wherein one or more drilling or completion parameters are adjusted in response to the resulting output signal.

B. A method that may include circulating a drilling fluid within a flow path that extends into and out of a borehole during drilling operations, generating a first output signal with a first optical computing device arranged near an outlet of the borehole, the first optical computing device having a first integrated computational element configured to optically interact with the drilling fluid, wherein the first output signal corresponds to a concentration of a gas present in the drilling fluid at the outlet, receiving the first output signal with a signal processor communicably coupled to the first optical computing device, determining the concentration of the gas present in the drilling fluid at the outlet of the borehole with the signal processor, whereby a resulting output signal is generated by the signal processor, conveying the resulting output signal to one or more peripheral devices such that a well operator is able to consider the resulting output signal, and adjusting one or more drilling or completion parameters in response to the resulting output signal.

Each of embodiments A and B may have one or more of the following additional elements in any combination: Element 1: wherein the gas is selected from the group comprising methane, ethane, propane, n-butane, n-pentane, iso-butane, iso-pentane, neo-pentane, benzene, toluene, carbon dioxide, carbon monoxide, hydrogen sulphide, acetic acid, argon, helium, oxygen, nitrogen, water, hydrogen, carbonyl sulfide, carbon disulfide, and any combination thereof. Element 2: further comprising a second optical computing device arranged at or near an inlet to the borehole and having a second integrated computational element configured to optically interact with the drilling fluid and generate a second output signal corresponding to the concentration of the gas present in the drilling fluid at the inlet. Element 3: wherein the signal processor is communicably coupled to the second optical computing device and configured to receive the second output signal and generate the resulting output signal corresponding to a difference between the first and second output signals, and wherein the one or more peripheral devices are configured to receive the resulting output signal and report to the well operator how the concentration of the gas changed between the inlet and the outlet. Element 4: wherein the one or more peripheral devices are configured to provide a graphical output depicting the concentration of the gas present in the drilling fluid at the outlet of the borehole. Element 5: wherein the graphical output comprises an output selected from the group consisting of one or more Pixler plots, Haworth plots, and gas ratio plots. Element 6: further comprising a choke valve arranged near the outlet, wherein the first optical computing device is arranged downhole from the choke valve. Element 7: further comprising an automated control system communicably coupled to the signal processor and configured to undertake one or more corrective actions in response to the resulting output signal.

Element 8: wherein the one or more peripheral devices comprise at least one of a monitor and a printer coupled to a computer system, and wherein conveying the resulting output signal to one or more peripheral devices comprises providing a graphical output of the resulting output signal for consideration by the well operator with the monitor or the printer. Element 9: wherein the one or more peripheral devices comprise an alarm, and wherein conveying the resulting output signal to one or more peripheral devices comprises alerting the well operator either audibly or visually with the alarm when the resulting output signal reports a gas concentration that exceeds a predetermined safe limit. Element 10: further comprising shutting down the well upon being alerted that the gas concentration exceeds the predetermined safe limit. Element 11: further comprising adding additives to the drilling fluid upon being alerted that the gas concentration exceeds the predetermined safe limit. Element 12: wherein adjusting the one or more drilling or completion parameters comprises altering geosteering of a drill bit. Element 13: wherein adjusting the one or more drilling or completion parameters comprises at least one of changing a cementing program, changing a casing program, changing a casing design, optimizing placement of downhole perforations, sliding sleeves, and slotted liners, and optimizing isolation of zones from which production is not required. Element 14: further comprising generating a second output signal with a second optical computing device arranged at or near an inlet to the borehole, the second optical computing device having a second integrated computational element configured to optically interact with the drilling fluid, wherein the second output signal corresponds to the concentration of the gas present in the drilling fluid at the inlet, receiving the second output signal with the signal processor communicably coupled to the second optical computing device, calculating a difference between the first and second output signals with the signal processor, whereby the resulting output signal is generated and correspond to how the concentration of the gas changed between the inlet and the outlet, and reporting the difference between the first and second output signals to the well operator with the one or more peripheral devices. Element 15: further comprising undertaking one or more corrective actions in response to the resulting output signal. Element 16: wherein undertaking the one or more corrective actions comprises at least one of shutting down the well and adding additives to the drilling fluid as directed by an automated control system communicably coupled to the signal processor.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively described herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A system, comprising:
a flow path circulating a drilling fluid into and out of a borehole during drilling operations, the flow path comprising a sampling window;
a first optical computing device arranged near the sampling window, the first optical computing device comprising:
a first integrated computational element configured to receive reflected electromagnetic radiation from the drilling fluid through the sampling window and generate a first output signal corresponding to a concentration of a gas present in the drilling fluid, wherein the first integrated computational element comprises multiple alternating layers of two materials having a different index of refraction, wherein a number of the alternating layers of two materials and a thickness of each of the alternating layers of two materials are selected based on an expected spectroscopic response of the gas present in the drilling fluid; and
a second integrated computational element comprising multiple alternating layers of two materials having different index of refraction and different number and thicknesses than the multiple alternating layers of the first integrated computational element, the second integrated computational element configured to provide a second output signal indicative of an absence of the gas in the drilling fluid;
a signal processor communicably coupled to the first optical computing device and configured to receive the first output signal and the second output signal and determine the concentration of the gas present in the drilling fluid, thereby resulting in a resulting output signal being generated by the signal processor; and
one or more peripheral devices communicably coupled to the signal processor and configured to receive the resulting output signal.

2. The system of claim 1, wherein the gas is selected from methane, ethane, propane, n-butane, n-pentane, iso-butane, iso-pentane, neo-pentane, benzene, toluene, carbon dioxide, carbon monoxide, hydrogen sulphide, acetic acid, argon, helium, oxygen, nitrogen, water, hydrogen, carbonyl sulfide, carbon disulfide, and any combination thereof.

3. The system of claim 1, further comprising a second optical computing device arranged at or near an inlet to the borehole and having a third integrated computational element configured to optically interact with the drilling fluid and generate a third output signal corresponding to the concentration of the gas present in the drilling fluid at the inlet.

4. The system of claim 3, wherein the signal processor is communicably coupled to the second optical computing device and configured to receive the third output signal and generate the resulting output signal based on the first output signal, the second output signal, and the third output signal, and wherein the one or more peripheral devices are configured to receive the resulting output signal and report a change in the concentration of the gas between the inlet and the sampling window.

5. The system of claim 1, wherein the one or more peripheral devices are configured to provide a graphical output depicting the concentration of the gas present in the drilling fluid.

6. The system of claim 5, wherein the graphical output comprises an output selected from the group consisting of one or more Pixler plots, Haworth plots, and gas ratio plots.

7. The system of claim 1, further comprising a choke valve, wherein the first optical computing device is arranged downhole from the choke valve.

8. The system of claim 1, further comprising an automated control system communicably coupled to the signal processor and configured to undertake one or more corrective actions in response to the resulting output signal.

9. A method, comprising:
circulating a drilling fluid within a flow path that extends into and out of a borehole during drilling operations, wherein the flow path comprises a sampling window;
generating a first output signal with a first optical computing device arranged near the sampling window, the first optical computing device having a first integrated computational element configured to receive reflected electromagnetic radiation from the drilling fluid through the sampling window, wherein the first output signal corresponds to a concentration of a gas present in the drilling fluid, wherein generating the first output signal comprises interacting the first integrated computational element with the reflected electromagnetic radiation to generate an output electromagnetic radiation having an intensity that is proportional to a product of a spectroscopic response of the reflected electromagnetic radiation with a regression vector associated with the gas present in the drilling fluid;
generating, with a second integrated computational element, a second output signal indicative of an absence of the gas in the drilling fluid;
receiving the first output signal and the second output signal with a signal processor communicably coupled to the first optical computing device;
determining the concentration of the gas present in the drilling fluid with the signal processor, whereby a resulting output signal is generated by the signal processor;
conveying the resulting output signal to one or more peripheral devices; and
adjusting one or more drilling or completion parameters in response to the resulting output signal.

10. The method of claim 9, wherein the one or more peripheral devices comprise at least one of a monitor and a printer coupled to a computer system, and wherein conveying the resulting output signal to one or more peripheral devices comprises providing a graphical output of the resulting output signal.

11. The method of claim 10, wherein the graphical output comprises an output selected from the group consisting of one or more Pixler plots, Haworth plots, and gas ratio plots.

12. The method of claim 9, wherein the one or more peripheral devices comprises an alarm, and wherein conveying the resulting output signal to one or more peripheral devices comprises alerting either audibly or visually with the alarm when the resulting output signal reports a gas concentration that exceeds a predetermined safe limit.

13. The method of claim 12, further comprising shutting down a well upon being alerted that the gas concentration exceeds the predetermined safe limit.

14. The method of claim 12, further comprising adding additives to the drilling fluid upon being alerted that the gas concentration exceeds the predetermined safe limit.

15. The method of claim 9, wherein adjusting the one or more drilling or completion parameters comprises altering a geosteering of a drill bit.

16. The method of claim 9, wherein adjusting the one or more drilling or completion parameters comprises at least one of changing a cementing program, changing a casing program, changing a casing design, optimizing placement of downhole perforations, sliding sleeves, and slotted liners, and optimizing isolation of zones from which production is not required.

17. The method of claim 9, further comprising:
generating a third output signal with a second optical computing device arranged at or near an inlet to the borehole, the second optical computing device having a third integrated computational element configured to optically interact with the drilling fluid, wherein the third output signal corresponds to the concentration of the gas present in the drilling fluid at the inlet;
receiving the third output signal with the signal processor communicably coupled to the second optical computing device;
calculating, with the signal processor, the resulting output signal based on the first output signal, the second output signal, and the third output signal, the resulting output signal corresponding to a change in the concentration of the gas between the inlet and the sampling window; and
reporting a difference between the first and second output signals resulting output signal to the one or more peripheral devices.

18. The method of claim 9, further comprising undertaking one or more corrective actions in response to the resulting output signal.

19. The method of claim 18, wherein undertaking the one or more corrective actions comprises at least one of shutting down a well and adding additives to the drilling fluid as directed by an automated control system communicably coupled to the signal processor.

20. The method of claim 9, wherein the gas is selected from methane, ethane, propane, n-butane, n-pentane, iso-butane, iso-pentane, neo-pentane, benzene, toluene, carbon dioxide, carbon monoxide, hydrogen sulphide, acetic acid, argon, helium, oxygen, nitrogen, water, hydrogen, carbonyl sulfide, carbon disulfide, and any combination thereof.

* * * * *